US010617395B2

(12) United States Patent
Yamamoto (10) Patent No.: US 10,617,395 B2
(45) Date of Patent: Apr. 14, 2020

(54) ULTRASOUND DIAGNOSTIC APPARATUS AND DOPPLER WAVEFORM IMAGE GENERATING METHOD (71) Applicant: FUJIFILM Corporation, Tokyo (JP)

(72) Inventor: Katsuya Yamamoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 705 days.

(21) Appl. No.: 15/234,710

(22) Filed: Aug. 11, 2016

(65) Prior Publication Data
US 2017/0049418 A1 Feb. 23, 2017

(30) Foreign Application Priority Data

Aug. 17, 2015 (JP) .................. 2015-160356

(51) Int. Cl.
*A61B 8/06* (2006.01)
*A61B 8/00* (2006.01)
(Continued)

(52) U.S. Cl.
CPC .............. *A61B 8/5207* (2013.01); *A61B 8/06* (2013.01); *A61B 8/14* (2013.01); *A61B 8/4488* (2013.01);
(Continued)

(58) Field of Classification Search
CPC .......... A61B 8/5207; A61B 8/06; A61B 8/14; A61B 8/4483; A61B 8/463; A61B 8/467;
(Continued)

(56) References Cited

U.S. PATENT DOCUMENTS 5,485,844 A * 1/1996 Uchibori ................. G01S 15/18
600/455
5,971,927 A * 10/1999 Mine ....................... A61B 8/06
600/455
(Continued)

FOREIGN PATENT DOCUMENTS

JP 6-327672 A 11/1994
JP 2003-79625 A 3/2003
(Continued)

OTHER PUBLICATIONS

J. Powers and F. Kremakau, "Medical ultrasound systems", 2011, Published Online May 18, 2011, Interface Focus, vol. 1, pp. 477-489.*
(Continued)

*Primary Examiner* — Patricia J Park
(74) *Attorney, Agent, or Firm* — Birch, Stewart, Kolasch & Birch, LLP (57) ABSTRACT

An ultrasound diagnostic apparatus includes a quadrature detection section configured to perform quadrature detection on reception radio-frequency data generated by a reception circuit to generate complex data, a frequency analyzer configured to perform a first frequency analysis using the complex data of a set number of sample points starting from a first start point and a second frequency analysis using at least one group of the complex data of the set number of sample points starting from a second start point that is different from the first start point, and to acquire a spectral signal corresponding to each pixel of a Doppler waveform image based on results of the first frequency analysis and the second frequency analysis, and a Doppler waveform image generator configured to generate the Doppler waveform image using the spectral signal.

9 Claims, 5 Drawing Sheets (51) Int. Cl.
  *A61B 8/08* (2006.01)
  *G01S 15/89* (2006.01)
  *A61B 8/14* (2006.01)
  *G01S 7/52* (2006.01)

(52) U.S. Cl.
  CPC .............. *A61B 8/463* (2013.01); *A61B 8/469* (2013.01); *A61B 8/488* (2013.01); *G01S 7/52046* (2013.01); *G01S 7/52066* (2013.01); *G01S 15/8915* (2013.01); *G01S 15/8979* (2013.01); *G01S 7/52074* (2013.01)

(58) Field of Classification Search
  CPC ......... A61B 8/488; A61B 8/5276; A61B 8/54; G01S 7/52046; G01S 7/52066; G01S 7/52085; G01S 15/8915; G01S 15/8979
  USPC ....................................................... 600/441
  See application file for complete search history.

(56) References Cited

U.S. PATENT DOCUMENTS

| | | | |
|---|---|---|---|
| 2003/0055333 A1 | 3/2003 | Amemiya et al. | |
| 2005/0080329 A1 | 4/2005 | Uchibori | |
| 2005/0222506 A1* | 10/2005 | Takimoto | A61B 8/06 600/455 |
| 2006/0084873 A1* | 4/2006 | Baba | A61B 8/06 600/441 |
| 2007/0167790 A1* | 7/2007 | Kim | A61B 8/08 600/454 |
| 2008/0114240 A1* | 5/2008 | Sasaki | A61B 8/06 600/440 |
| 2010/0099990 A1* | 4/2010 | Lee | A61B 8/06 600/453 |
| 2013/0006111 A1* | 1/2013 | Sasaki | A61B 8/0891 600/441 |
| 2014/0086014 A1* | 3/2014 | Kobayashi | G01S 7/52066 367/90 |

FOREIGN PATENT DOCUMENTS

| | | |
|---|---|---|
| JP | 2005-46194 A | 2/2005 |
| JP | 2006-141996 A | 6/2006 |

OTHER PUBLICATIONS

J. L. Enriquex and T. S. Wu, "An introduction to ultrasound equipment and knobology", 2014, Critical Care Clinics, vol. 30, pp. 25-45.*

Kai E. Thomenius, "Evolution of ultrasound beamformers", Nov. 3, 1996, Proceedings 1996 IEEE Ultrasonics Symposium, pp. 1615-1662.*

Japanese Office Action, dated Jun. 5, 2018, for Japanese Application No. 2015-160356, along with an English machine translation.

Extended European Search Report for European Application No. 16183089.8, dated Dec. 16, 2016.

* cited by examiner

ULTRASOUND DIAGNOSTIC APPARATUS AND DOPPLER WAVEFORM IMAGE GENERATING METHOD

CROSS-REFERENCE TO RELATED APPLICATIONS

The present application claims priority under 35 U.S.C. § 119 to Japanese Patent Application No. 2015-160356, filed on Aug. 17, 2015. The above application is hereby expressly incorporated by reference, in its entirety, into the present application.

BACKGROUND OF THE INVENTION

The present invention relates to an ultrasound diagnostic apparatus and a method for generating a Doppler waveform image and particularly to an ultrasound diagnostic apparatus for generating a Doppler waveform image through the pulsed Doppler technique or continuous wave Doppler technique.

Conventionally, an ultrasound diagnostic apparatus using ultrasound images has been in a practical use in the medical field. In general, this type of ultrasound diagnostic apparatus comprises an ultrasound probe having a built-in transducer array and an apparatus body connected to the ultrasound probe. The ultrasound probe transmits an ultrasonic beam toward the inside of a subject's body and receives ultrasonic echoes from the subject, and the apparatus body electrically processes the reception signals to generate a B-mode (brightness mode) image.

In addition, for the purpose of obtaining blood flow information, an approach where a Doppler waveform image is generated through the pulsed Doppler technique or the like and displayed with a B-mode image on a display has been adopted.

Accordingly, an ultrasound diagnostic apparatus that performs Doppler processing together with B-mode processing has been disclosed in JP2003-79625A, for example.

In the pulsed Doppler technique, using a transducer array, transmittance of an ultrasonic pulse toward a subject's body and reception of an ultrasonic echo from the subject are repeated at intervals of the pulse repetition frequency (PRF). A reception signal obtained from the transducer array at each transmission and reception of an ultrasonic wave is subjected to phasing addition and thereafter converted into complex data containing a Doppler component through quadrature detection, and the complex data at sample points obtained in a predetermined time width is Fourier-transformed, whereby a spectral signal is acquired. Fourier transformation is continuously carried out at intervals of a predetermined number of sample points, and a Doppler waveform image representing changes in the flow rate with respect to the time axis is generated based on acquired spectral signals.

However, due to interferences between speckle signals or Doppler signals themselves occurring in transmission and reception of ultrasonic waves, for example, black lines appear in a Doppler waveform image thus generated, leading to deterioration of image quality.

Accordingly, a Doppler waveform image data has been conventionally subjected to smoothing treatment in the time direction and the frequency direction to thereby obscure the black lines.

However, the resolution would deteriorate in the time direction as smoothing treatment is performed, whereas the time resolution would deteriorate if it is attempted to improve the image quality. Reversely, if deterioration of the time resolution is suppressed, the black lines would stand out, deteriorating the image quality. This has been a problem.

SUMMARY OF THE INVENTION

The present invention has been made to solve the above-described problem of the prior art and has an object to provide an ultrasound diagnostic apparatus and a Doppler waveform image generating method that can suppress generation of black lines in a Doppler waveform image without a decrease in the time resolution to thereby improve the image quality.

An ultrasound diagnostic apparatus according to the present invention comprises:

a transducer array;

a transmission circuit configured to transmit an ultrasonic beam from the transducer array toward a subject, a reception circuit configured to process a reception signal outputted from the transducer array having received ultrasonic echoes from the subject to generate reception radio-frequency data that has undergone phasing addition, a quadrature detection section configured to perform quadrature detection on the reception radio-frequency data generated by the reception circuit to generate complex data, a frequency analyzer configured to perform a first frequency analysis using the complex data of a set number of sample points starting from a first start point and a second frequency analysis using at least one group of the complex data of the set number of sample points starting from a second start point that is different from the first start point, and to acquire a spectral signal corresponding to each pixel of a Doppler waveform image based on results of the first frequency analysis and the second frequency analysis, and a Doppler waveform image generator configured to generate the Doppler waveform image using the spectral signal.

A method for generating a Doppler waveform image according to the present invention comprises the steps of:

transmitting an ultrasonic beam from a transducer array toward a subject, generating reception radio-frequency data that has undergone phasing addition by processing reception signal outputted from the transducer array having received an ultrasonic echo from the subject, generating complex data by performing quadrature detection on the reception radio-frequency data, performing a first frequency analysis using the complex data of a preliminarily set number of sample points starting from a first start point and a second frequency analysis using at least one group of complex data of the preliminarily set number of sample points starting from a second start point that is different from the first start point to acquire a spectral signal corresponding to each pixel of a Doppler waveform image based on results of the first frequency analysis and the second frequency analysis, and generating the Doppler waveform image using the spectral signal.

DETAILED DESCRIPTION OF THE INVENTION

Embodiments of the invention will be described below based on the appended drawings.

Embodiment 1

Figure 1:
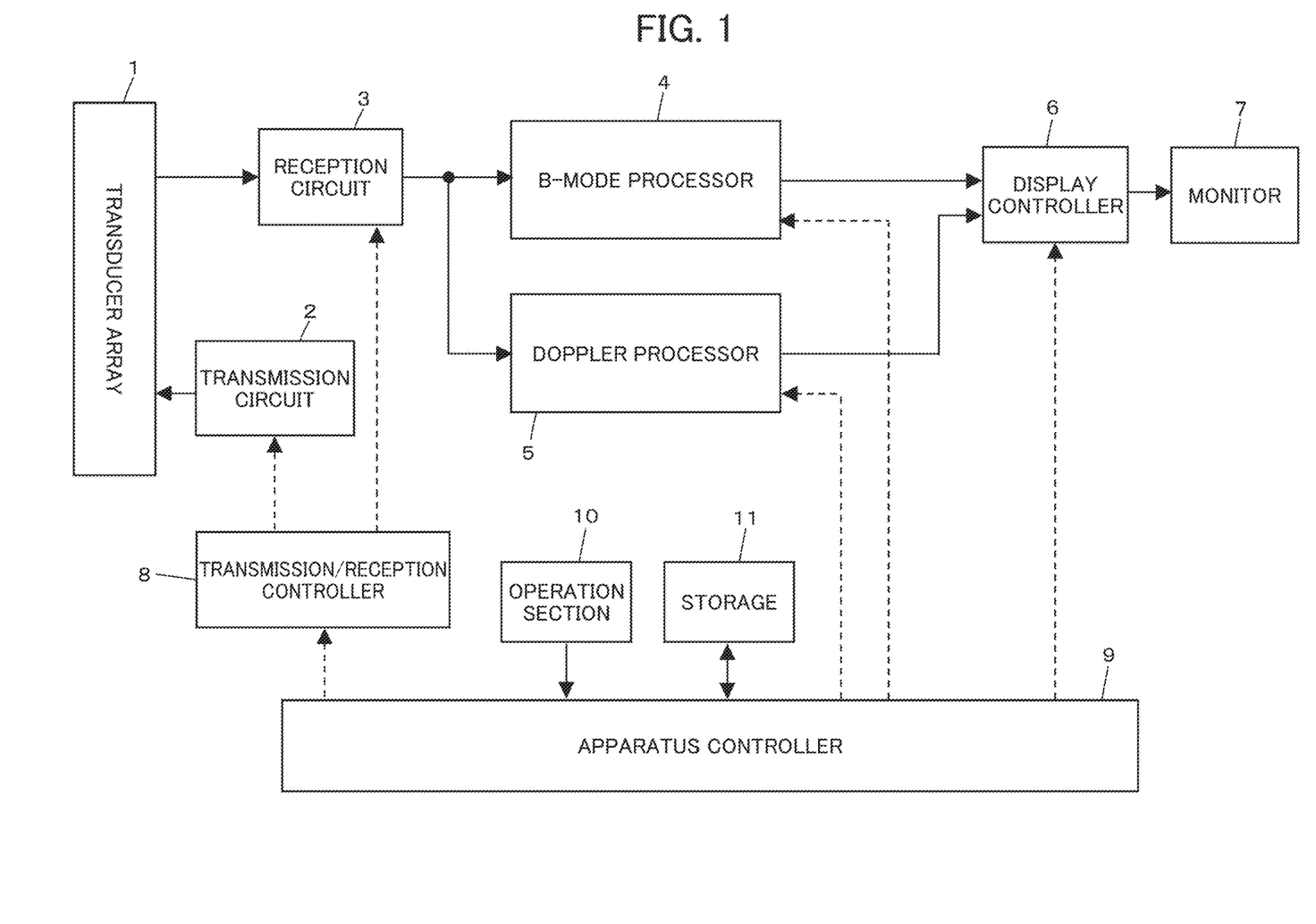
FIG. 1 is a block diagram illustrating a configuration of an ultrasound diagnostic apparatus according to an embodiment 1 of the invention.

FIG. 1 illustrates a configuration of an ultrasound diagnostic apparatus according to an embodiment 1 of the invention. The ultrasound diagnostic apparatus includes a transducer array 1, a transmission circuit 2 and a reception circuit 3, the circuits being connected to the transducer array 1. To the reception circuit 3, a B-mode processor 4 and a Doppler processor 5 are connected in parallel, and a monitor 7 is connected to the B-mode processor 4 and the Doppler processor 5 via a display controller 6.

A transmission/reception controller 8 is connected to the transmission circuit 2 and the reception circuit 3, and an apparatus controller 9 is connected to the B-mode processor 4, the Doppler processor 5, the display controller 6 and the transmission/reception controller 8. In addition, an operation section 10 and a storage 11 are connected to the apparatus controller 9.

The transducer array 1 includes a plurality of ultrasound transducers arranged one-dimensionally or two-dimensionally. The ultrasound transducers transmit ultrasonic waves according to actuation signals supplied from the transmission circuit 2 and receive ultrasonic echoes from the subject to output reception signals. Each of the ultrasound transducers comprises an oscillator composed of a piezoelectric body and electrodes each provided on either end of the piezoelectric body. The piezoelectric body is composed of, for example, a piezoelectric ceramic represented by a lead zirconate titanate (PZT), a piezoelectric polymer represented by polyvinylidene fluoride (PVDF), or a piezoelectric monocrystal represented by lead magnesium niobate-lead titanate solid solution (PMN-PT).

When the electrodes of each of the oscillators are supplied with a pulsed voltage or a continuous-wave voltage, the piezoelectric body expands and contracts to cause the oscillator to generate pulsed or continuous ultrasonic waves. These ultrasonic waves are synthesized to form an ultrasonic beam. Besides, the oscillators receive propagating ultrasonic waves to contract, thereby generating electric signals, which will be outputted as reception signals of the ultrasonic waves.

The transmission circuit 2 includes, for example, a plurality of pulsars and adjusts the delay amounts for actuation signals based on a transmission delay pattern selected according to a control signal transmitted from the transmission/reception controller 8 so that the ultrasonic waves transmitted from a plurality of ultrasound transducers of the transducer array 1 form an ultrasonic beam and supplies the ultrasound transducers with delay-adjusted actuation signals.

Figure 2:
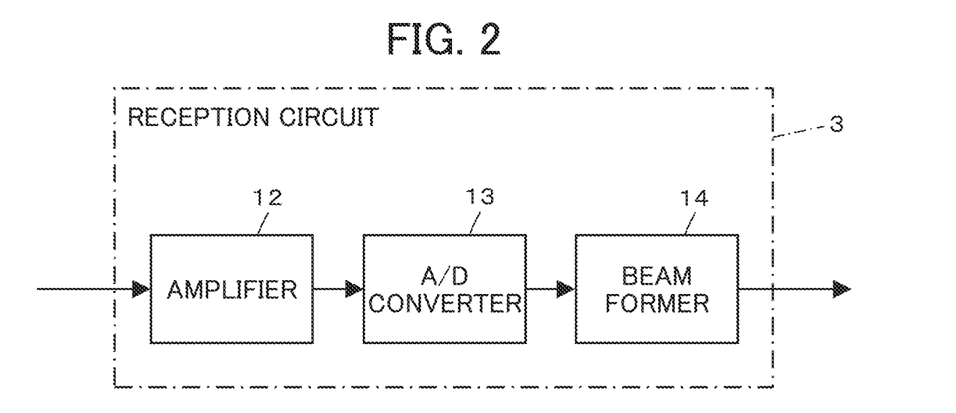
FIG. 2 is a block diagram illustrating an internal configuration of a reception circuit in the embodiment 1.

As illustrated in FIG. 2, the reception circuit 3 has a structure in which an amplifier 12, an analog-to-digital converter (A/D) converter 13, and a beam former 14 are connected in series. The reception circuit 3 causes the amplifier 12 and the A/D converter 13 to amplify and A/D-convert the reception signals transmitted from the ultrasound transducers of the transducer array 1, and then causes the beam former 14 to perform reception focusing processing by providing the reception signals with respective delays according to the sound speed or sound speed distribution that is set based on a reception delay pattern selected according to the control signal from the transmission/reception controller 8 and adding them up. The reception focusing processing generates a reception radio-frequency data that has undergone phasing addition and has narrower focal points of ultrasonic echoes.

Figure 3:
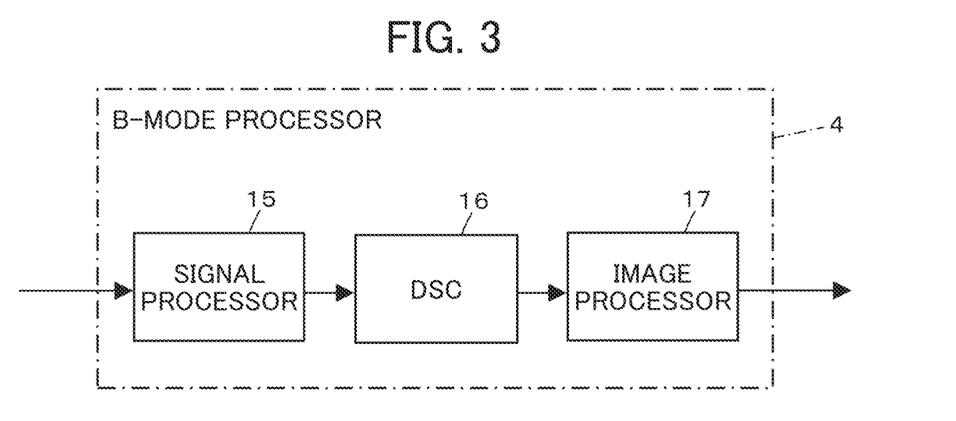
FIG. 3 is a block diagram illustrating an internal configuration of a B-mode processor in the embodiment 1.

As illustrated in FIG. 3, the B-mode processor 4 has a structure in which a signal processor 15, a Digital Scan Converter (DSC) 16 and an image processor 17 are connected in series.

The signal processor 15 corrects the reception radio-frequency data generated by the reception circuit 3 in terms of attenuation caused due to distance based on the depth at which the ultrasonic waves are reflected, and then performs envelope detection processing to thereby generate a B-mode image signal which is tomographic image information on a tissue inside the subject.

The DSC 16 converts the B-mode image signal generated by the signal processor 15 into an image signal compatible with an ordinary television signal scanning mode (raster conversion).

The image processor 17 performs various types of necessary image processing such as gradation processing on the B-mode image signal entered from the DSC 16 and then outputs the B-mode image signal to the display controller 6.

Figure 4:
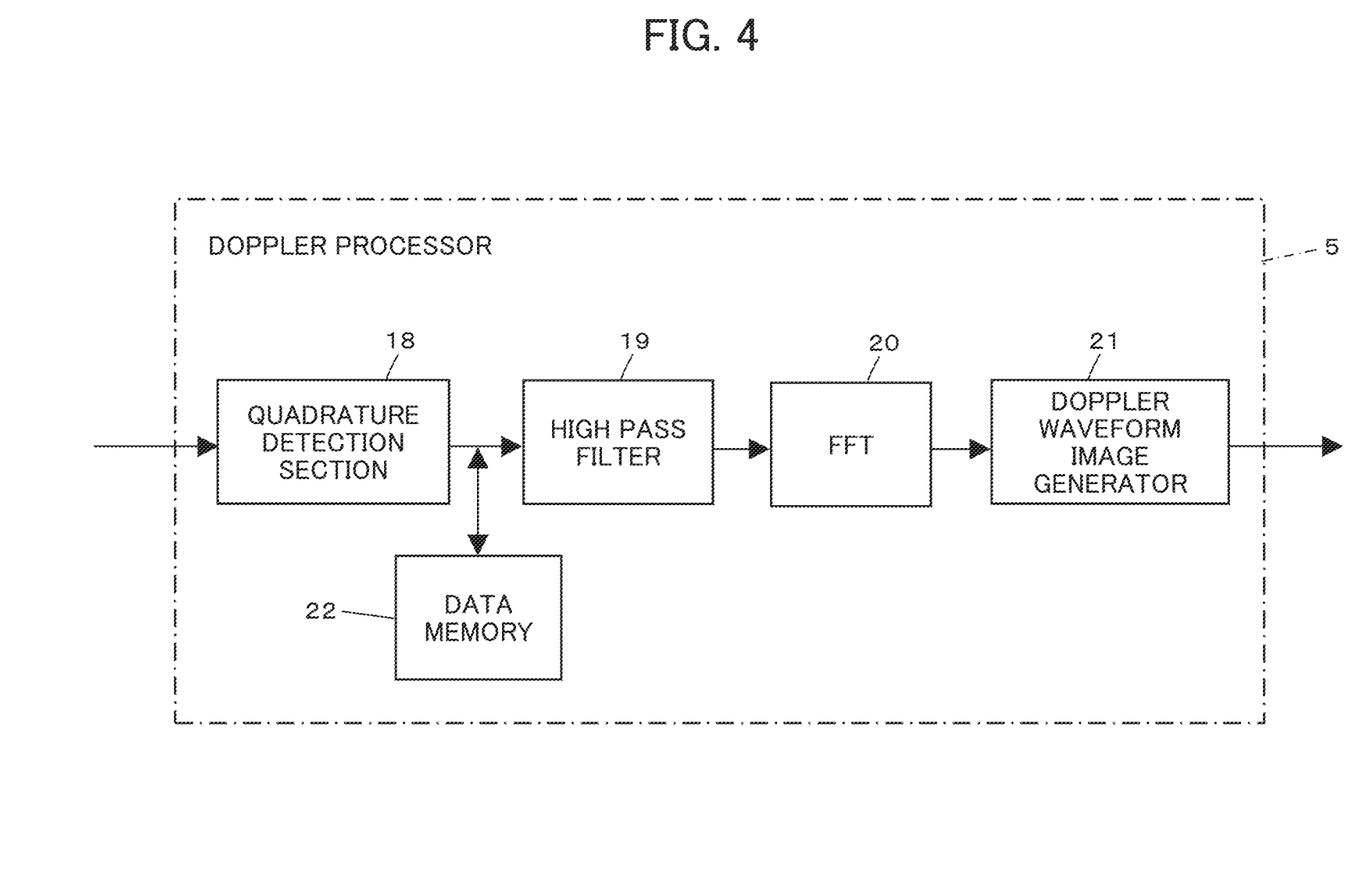
FIG. 4 is a block diagram illustrating an internal configuration of a Doppler processor in the embodiment 1.

The Doppler processor 5 generates a Doppler waveform image through the so-called pulsed Doppler technique and, as illustrated in FIG. 4, has a structure in which a quadrature detection section 18, a high pass filter 19, a Fast Fourier Transformer (FFT) 20 and a Doppler waveform image generator 21 are connected in series, and a data memory 22 is connected to an output terminal of the quadrature detection section 18.

The quadrature detection section 18 converts the reception radio-frequency data into complex data through quadrature detection, by combining the reception radio-frequency data generated by the reception circuit 3 with a carrier signal of a reference frequency.

The high pass filter 19 functions as a so-called wall filter and removes a frequency component derived from motion of a tissue in the subject's body from the complex data generated by the quadrature detection section 18.

The FFT 20 performs frequency analysis on the complex data including a plurality of sample points through Fourier transformation, thereby generating a spectral signal.

The Doppler waveform image generator 21 represents the spectral signal generated by the FFT 20 disposed along the time axis and represents a magnitude of each frequency component as brightness, whereby a Doppler waveform image signal is generated. In a Doppler waveform image, a horizontal axis represents the time axis, a vertical axis represents a Doppler shift frequency, i.e., flow velocity, and brightness of a waveform represents a power of each frequency component.

The data memory 22 stores the complex data to which the reception radio-frequency data was converted by the quadrature detection section 18.

The display controller 6 causes the monitor 7 to display a B-mode image based on the B-mode image signal generated by the B-mode processor 4 and to display a Doppler waveform image based on the Doppler waveform image signal generated by the Doppler processor 5 in the pulsed Doppler mode.

The monitor 7 includes a display device such as an LCD, for example, and displays the B-mode image and the Doppler waveform image under the control of the display controller 6.

The transmission/reception controller 8 controls the transmission circuit 2 and the reception circuit 3 such that transmission of an ultrasonic pulse to the subject and reception of an ultrasonic echo from the subject are repeated at intervals of the pulse repetition frequency (PRF) based on the various control signals sent by the apparatus controller 9.

The apparatus controller 9 controls the B-mode processor 4, the Doppler processor 5, the display controller 6 and the transmission/reception controller 8 based on an instruction input by an operator through the operation section 10. The FFT 20 of the Doppler processor 5 and the apparatus controller 9 constitute a frequency analyzer.

The operation section 10 is provided for the operator to perform input operations and may be composed of, for example, a keyboard, a mouse, a track ball, and/or a touch panel.

The storage 11 stores, for example, an operation program and may be constituted by, for example, a recording medium such as a hard disc, a flexible disk, an MO (Magneto-Optical Disk), an MT (Magnetic Tape), a RAM (Random Access Memory), a CD-ROM (Compact Disk Read Only Memory), a DVD-ROM (Digital Versatile Disk Read Only Memory), an SD card (Secure Digital Card), a CF card (Compact Flash Card), or a USB memory (Universal Serial Bus Memory), or a server.

Each of the B-mode processor 4, the Doppler processor 5, the display controller 6, the transmission/reception controller 8 and the apparatus controller 9 is formed by using a CPU and an operation program causing the CPU to execute various kinds of processing. However, these may be formed by using digital circuits. Also, the B-mode processor 4, the Doppler processor 5, the display controller 6, the transmission/reception controller 8 and the apparatus controller 9 may be constituted by partially or totally integrated into a single CPU.

Here, the operation of the FFT 20 in the Doppler processor 5 will be described referring to FIG. 5.

Under the control of the apparatus controller 9, the FFT 20 performs frequency analysis through Fourier transformation on complex data Diq of a sample point group S0 consisting of a plurality of sample points starting from a first start point, among complex data Diq repeatedly obtained at intervals of the pulse repetition frequency (PRF), and, in addition to the sample point group S0, performs frequency analysis also on complex data Diq of sample point groups S1 to S4 each consisting of a plurality of sample points starting from the second start point that is different from the first start point.

The sample point groups S0 to S4 each include a preliminarily set number of sample points Nf. The sample point group S1 was obtained temporally earlier than the sample point group S0 by a number of sample points Nb, and the sample point group S2 was obtained temporally earlier than the sample point group S1 further by a number of sample points Nb. In addition, the sample point group S3 was obtained temporally later than the sample point group S0 by a number of sample points Nb, and the sample point group S4 was obtained temporally later than the sample point group S3 further by a number of sample points Nb.

The FFT 20 acquires a single spectral signal corresponding to a pixel $P_x$ based on a result of a first frequency analysis on the sample point group S0 and a result of a second frequency analysis on the sample point groups S1 to S4. In this process, the FFT 20 performs maximum value processing on the result of the first frequency analysis on the sample point group S0 and on the result of the second frequency analysis on the sample point groups S1 to S4, i.e., extracts the maximum power value of respective frequency components in each of the analysis results, whereby the FFT 20 can acquire the spectral signal corresponding to the pixel $P_x$.

Alternatively, the FFT 20 may perform averaging processing on the result of the first frequency analysis on the sample point group S0 and on the second frequency analysis on the sample point groups S1 to S4, i.e., calculate the average power value of respective frequency components in each of the analysis results to acquire the spectral signal corresponding to the pixel $P_x$.

Following the acquisition of the spectral signal corresponding to the pixel $P_x$, the FFT 20 acquires a spectral signal corresponding to a pixel $P_{x+1}$ adjacent to the pixel $P_x$ in the similar manner. That is, for the pixel $P_{x+1}$, the FFT 20 carries out not only the first frequency analysis on the complex data Diq of the sample point group S0 having the set number of sample points Nf starting from the first start point but also the second frequency analysis on the complex data Diq of the sample point groups S1 to S4 each having the set number of sample points Nf starting from the second start point that is different from the first start point and acquires a single spectral signal corresponding to the pixel $P_{x+1}$ based on the results of the first and second frequency analyses.

The first start point for the pixel $P_x$ and the first start point for the pixel $P_{x+1}$ are distanced from each other by the number of sample points Np corresponding to a gap between adjacent pixels.

Accordingly, spectral signals respectively corresponding to the pixels of a Doppler waveform image are acquired. FIG. 5 shows examples of the spectral signals respectively corresponding to the five pixels $P_{x-2}$ to $P_{x+2}$.

In an example, when the pulse repetition frequency (PRF) is 5,000 Hz, the sweep time Ts of the Doppler waveform image displayed on the monitor 7 is four seconds, the number of pixels PN along the time axis of the Doppler waveform image is 640, and the set number of sample points Nf on which the frequency analysis is performed is 128, the number of sample points Np corresponding to a gap between adjacent pixels is expressed as Np=5,000×4/640=31.

In addition, a number of sample points Nb between adjacent sample point groups S0 to S4 may be an arbitrary value from the minimum value $Nb_{MIN}=1$ to the maximum value $Nb_{MAX}$. The maximum value $Nb_{MAX}$ is expressed by the following formula.

$$Nb_{MAX} = Mp_{MAX}/2 < (PRF_{MAX} \times Ts_{MAX}/PN)/2$$

In the formula, $Np_{MAX}$ represents the maximum value of the number of sample points NP, $PRF_{MAX}$ represents the maximum value of the pulse repetition frequency PRF, $Ts_{MAX}$ represents the maximum value of the sweep time Ts of the Doppler waveform image, and PN represents the number of pixels along the time axis of the Doppler waveform image.

For example, when the maximum value $Ts_{MAX}$ of the sweep time Ts is 10 seconds, the maximum value $PRF_{MAX}$ of the pulse repetition frequency PRF is 15.6 kHz, and the maximum value $Np_{MAX}$ of the number of sample points Np is 244, the maximum value $Nb_{MAX}$ of the number of sample points $Nb=Np_{MAX}/2=122$ is established.

Meanwhile, a value of a gap 2×Nb between the sample point group S2 or S4 and the sample point group S0 is preferably set to a value smaller than ½ of the number of sample points Np corresponding to the gap between adjacent pixels, the sample point group S2 or S4 being farthest from the sample point group S0 among sample point groups S1 to S4 surrounding the sample point group S0.

Figure 5:
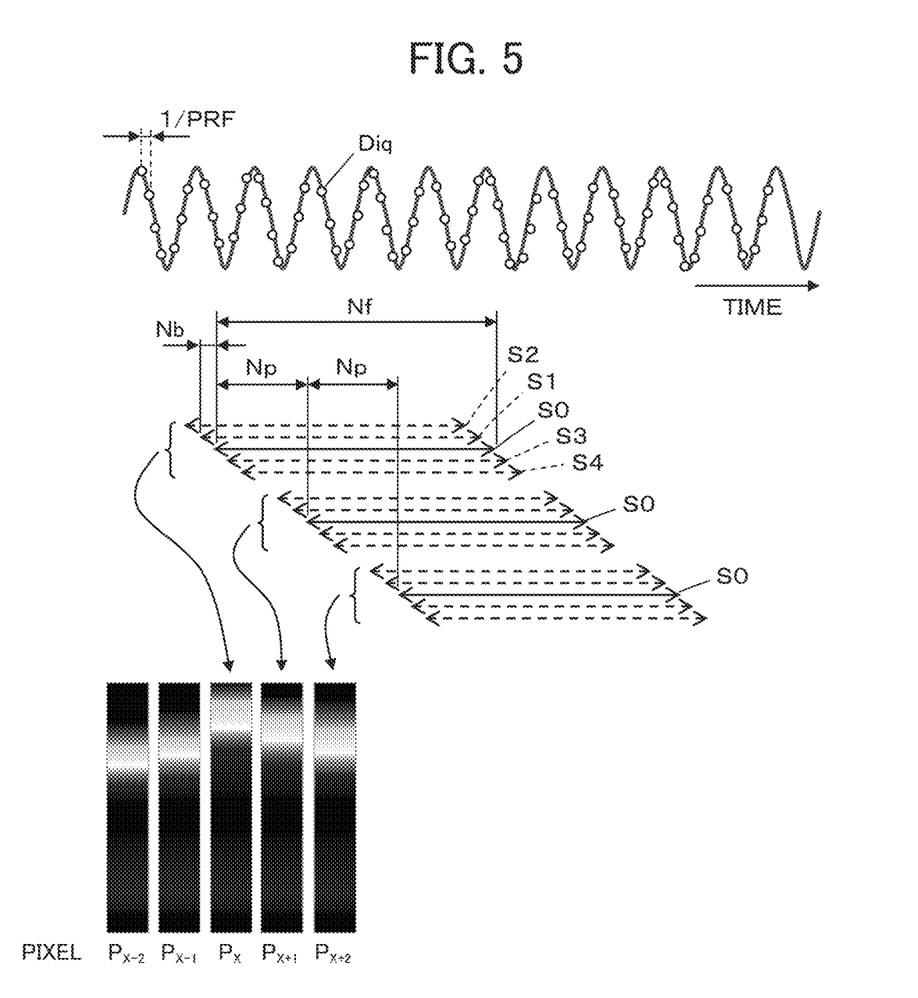
FIG. 5 is a diagram illustrating frequency analysis processing carried out by a FFT in the Doppler processor in the embodiment 1.

In FIG. 5, two sample point groups S1 and S2 that were obtained temporally earlier than the sample point group S0 and two sample point groups S3 and S4 that were obtained temporally later than the sample point group S0 are used as the sample point groups on which the second frequency analysis is performed. However, the number of sample point groups Ng on which the second frequency analysis is performed may be appropriately selected. In addition, the number of sample point groups obtained temporally earlier than the sample point group S0 and the number of sample point groups obtained temporally later than the sample point group S0 do not have to be same but may be different from each other.

The pulse repetition frequency PRF, the sweep time of the Doppler waveform image, the set number of sample points Nf on which the frequency analysis is performed, the number of sample points Nb between adjacent sample point groups, the number of surrounding sample point groups Ng on which the frequency analysis is performed and the acquisition method (maximum value processing or averaging processing) to acquire a single spectral signal corresponding to each pixel based on the results of first and second frequency analyses can be input into the apparatus controller 9 through the operation section 10.

Next, described is an operation of the ultrasound diagnostic apparatus according to the embodiment 1.

First, according to the actuation signal from the transmission circuit 2, a plurality of ultrasound transducers of the transducer array 1 transmit an ultrasonic beam, and the ultrasound transducers having received ultrasound echoes from a subject output reception signals to the reception circuit 3, the amplifier 12 amplifies the reception signals, which are subsequently A/D converted by the A/D converter 13 and then subjected to phasing addition at the beam former 14, whereby reception radio-frequency data is generated. The reception radio-frequency data is subjected to envelop detection processing by the signal processor 15 in the B-mode processor 4 to turn into a B-mode image signal, which is outputted to the display controller 6 via the DSC 16 and the image processor 17, whereupon the display controller 6 causes the monitor 7 to display the B-mode image.

Figure 6:
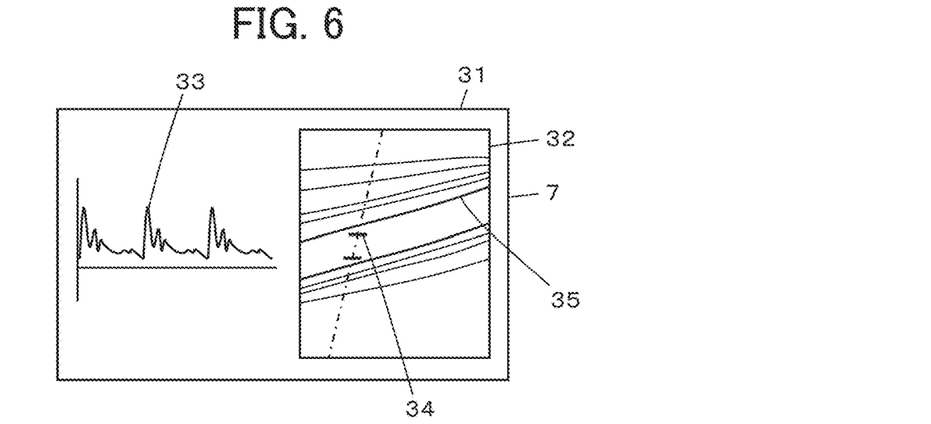
FIG. 6 is a diagram illustrating a display image in a pulsed Doppler mode.

Here, when an operator operates the operation section 10 and selects the pulsed Doppler mode, as illustrated in FIG. 6, a screen 31 of the monitor 7 is divided into two regions of a B-mode image 32 and a Doppler waveform image 33, and a gate 34 is displayed so as to be superimposed on the B-mode image 32. The gate 34 can move freely on the B-mode image 32 through the operation of the operation section 10, which is, for example, operated such that the gate 34 is positioned on a blood vessel 35 in order to measure a blood flow rate in the blood vessel 35 in the carotid arteries displayed in the B-mode image 32.

Here, it is assumed that the pulse repetition frequency PRF, the sweep time of the Doppler waveform image, the set number of sample points Nf, the number of sample points Nb between adjacent sample point groups, the number of sample point groups Ng on which the second frequency analysis is performed and the acquisition method (maximum value processing or averaging processing) to acquire a single spectral signal corresponding to each pixel based on the results of the first and second frequency analyses are preliminarily set in the apparatus controller 9 through the operation section 10.

Upon transmission of information on the position of the gate 34 from the apparatus controller 9 to the transmission/reception controller 8, the transmission/reception controller 8 controls the transmission circuit 2 and the reception circuit 3, whereby transmission of an ultrasonic pulse toward a specific direction, which passes the gate 34, and reception of an ultrasonic echo are repeated at intervals according to the pulse repetition frequency (PRF).

The reception radio-frequency data generated in the reception circuit 3 is converted into complex data by the quadrature detection section 18 in the Doppler processor 5, is stored in the data memory 22, and is outputted to the FFT 20 after frequency components derived from motions of body tissues in a subject are removed therefrom by the high pass filter 19.

The FFT 20 performs, based on the preliminarily set number of sample points Nf, the number of sample points Nb between adjacent sample point groups, the number of sample point groups Ng on which the second frequency analysis is performed, and the acquisition method for acquiring a spectral signal, the first frequency analysis using the complex data Diq in a single sample point group having the set number of sample points Nf from the first staring point and the second frequency analysis using the complex data Diq in the number of sample point groups Ng having the set number of sample points Nf each starting from the second start point, and acquires a spectral signal corresponding to each pixel based on the results of the first and second frequency analyses.

The Doppler waveform image generator 21 then generates a Doppler waveform image signal based on the spectral signals acquired by the FFT 20, and as illustrated in FIG. 6, the display controller 6 causes the monitor 7 to display the Doppler waveform image 33 in the screen 31. The horizontal axis represents the time axis of the Doppler waveform image 33, while the vertical axis represents a blood flow rate in the blood vessel 35. At this time, the Doppler waveform image signal generated from the spectral signal corresponding to each pixel does not undergo smoothing treatment either in the time direction or the frequency direction, and the Doppler waveform image 33 is displayed based on the Doppler waveform image signal generated by the Doppler waveform image generator 21.

Since transmission and reception of an ultrasonic beam for acquiring a B-mode image and transmission and reception of an ultrasonic beam for acquiring a Doppler waveform image are performed in a time-division manner, the B-mode image 32 and the Doppler waveform image 33 can be simultaneously displayed in the screen 31 of the monitor 7.

As described above, since the FFT 20 under the control of the apparatus controller 9 performs, for each pixel, not only the first frequency analysis for frequency-analyzing complex data Diq in a single sample point group having the set number of sample points Nf starting from the first start point but also the second frequency analysis for frequency-analyzing complex data Diq in the number of sample point groups Ng each having the set number of sample points Nf starting from the second start point that is different from the first start point, and acquires a spectral signal corresponding to each pixel based on the results of the first and second frequency analyses, the necessity of smoothing treatment on image data of a Doppler waveform image conventionally required can be removed, whereby generation of black lines in a Doppler waveform image can be suppressed while the time resolution is prevented from decreasing.

Figure 7A:
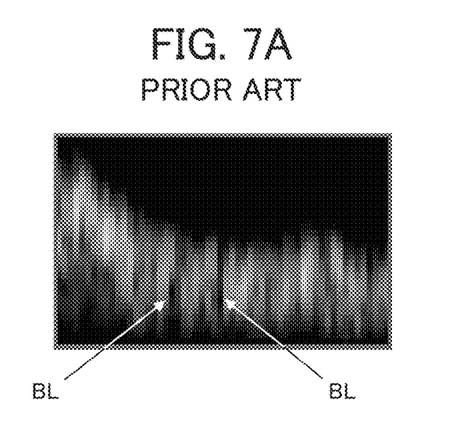
FIG. 7A illustrates a conventional Doppler waveform image generated from an image data that has undergone smoothing treatment in the time direction.

In particular, illustrated in FIG. 7A is a Doppler waveform image generated by the conventional method where frequency analysis is performed only on complex data Diq of the set number of sample points Nf starting from the first start point, not on the set number of sample points Nf starting from the second start point that is different from the first start point. In this example, the pulse repetition frequency PRF is set to 5,000 Hz, the sweep time of the Doppler waveform image to four seconds, the number of pixels along the time axis of the Doppler waveform image to 640, and the set number of sample points Nf used for frequency analysis to 128.

It is apparent that black lines BL appear in the Doppler waveform image.

Figure 7B:
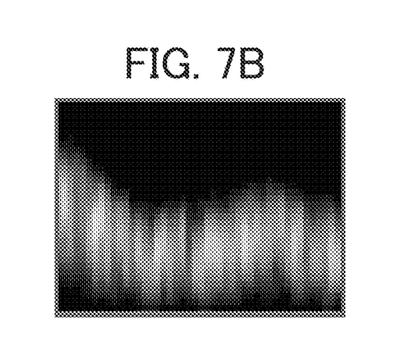
FIG. 7B illustrates a Doppler waveform image generated in the embodiment 1.

On the other hand, illustrated in FIG. 7B is a Doppler waveform image generated by the method of the embodiment 1 where, having the pulse repetition frequency PRF, the sweep time of the Doppler waveform image, the number of pixels along the time axis of the Doppler waveform image, and the set number of sample points Nf used for frequency analysis being same as those in the case of FIG. 7A, the first frequency analysis using complex data Diq in the sample point group S0 having the set number of sample points Nf starting from the first start point, and the second frequency analysis using complex data Diq in the sample point groups S1 to S4 each having the set number of sample points Nf starting from the second start point that is different from the first start point are carried out.

It is apparent that the black lines BL appearing in FIG. 7A have become obscure.

As described above, according to the invention, generation of black lines can be suppressed, and the image quality can be improved, without decrease in the time resolution.

In addition, since the complex data converted by the quadrature detection section 18 in the Doppler processor 5 is stored in the data memory 22, by changing at least one of the set number of sample points Nf to be used for frequency analysis, the number of sample points Nb between adjacent sample point groups, and the number of sample point groups Ng on which the second frequency analysis is performed and inputting the changed number through the operation section 10, a new Doppler waveform image can be generated under the changed condition.

Embodiment 2

Figure 8:
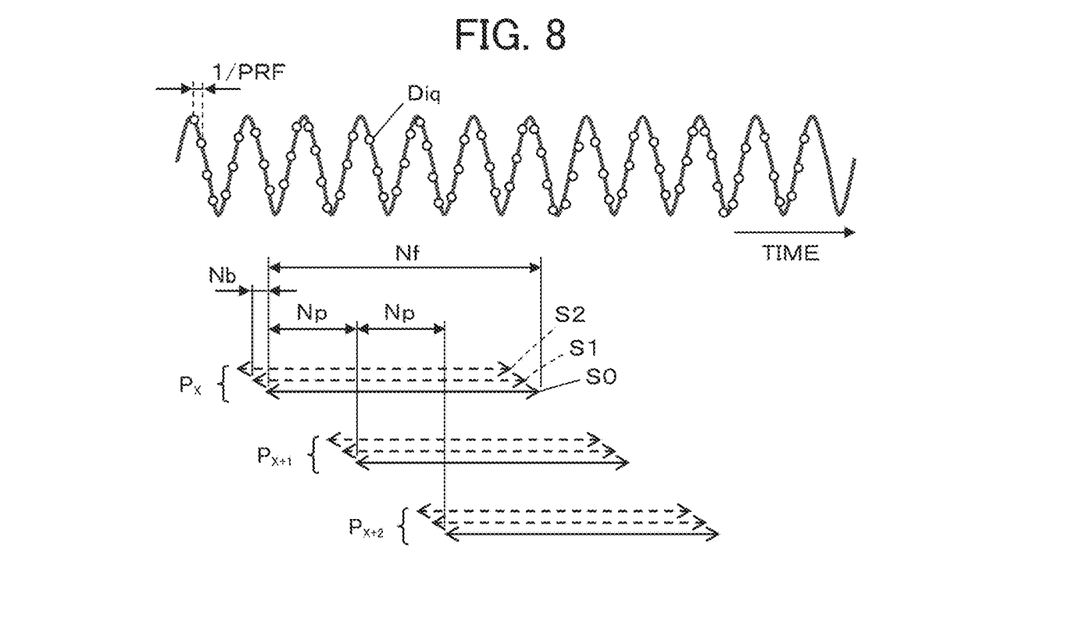
FIG. 8 is a diagram illustrating frequency analysis processing carried out by the FFT in the Doppler processor in an embodiment 2.

In the embodiment 1 described above, two sample point groups S1 and S2 obtained temporally earlier than the sample point group S0 and two sample point groups S3 and S4 obtained temporally later than the sample point group S0 on which the first frequency analysis is performed are used in the second frequency analysis. However, as illustrated in FIG. 8, two sample point groups S1 and S2 obtained temporally earlier than the sample point group S0 may be only used for the second frequency analysis to acquire a single spectral signal corresponding to each pixel based on the results of the first and the second frequency analyses. In this manner, also, generation of black lines can be suppressed, and the image quality may be improved without decrease in the time resolution.

In addition, one or three or more sample point groups obtained temporally earlier than the sample point group S0 on which the first frequency analysis is performed may be used as sample point groups for the second frequency analysis.

Similarly, one or more sample point groups obtained temporally later than the sample point group S0 on which the first frequency analysis is performed may be used for the second frequency analysis.

What is claimed is:
1. An ultrasound diagnostic apparatus comprising:
a transducer array;
a transmission circuit configured to transmit an ultrasonic beam from the transducer array toward a subject,
a reception circuit configured to process a reception signal outputted from the transducer array having received ultrasonic echoes from the subject to generate reception radio-frequency data that has undergone phasing addition,
a Doppler processor configured
to perform quadrature detection on the reception radio-frequency data generated by the reception circuit to generate complex data;
to perform a first frequency analysis using the complex data of a first sample point group that includes a set number of sample points starting from a first start point and a second frequency analysis using the complex data of at least one second sample point group that includes the set number of sample points starting from a second start point that is different from the first start point;
to acquire a spectral signal corresponding to each pixel of a Doppler waveform image based on results of the first frequency analysis and the second frequency analysis; and
to generate the Doppler waveform image using the spectral signal, and
a monitor configured to display the Doppler waveform image generated by the Doppler processor,
wherein the first start point for one pixel and the first start point for another pixel adjacent to the one pixel are distanced from each other by a first number of sample points corresponding to a first gap between adjacent pixels, and
wherein a second number of sample points corresponding to a second gap between the first sample point group and one of the at least one second sample point group farthest from the first sample point group for each pixel is set to a value smaller than ½ of the first number of sample points.

2. The ultrasound diagnostic apparatus according to claim 1, wherein the Doppler processor extracts a maximum power value of respective frequency components in the results of the first frequency analysis and the second frequency analysis to thereby acquire the spectral signal corresponding to the each pixel.

3. The ultrasound diagnostic apparatus according to claim 1, wherein the Doppler processor calculates an average power value of respective frequency components in the results of the first frequency analysis and the second frequency analysis to thereby acquire the spectral signal corresponding to the each pixel.

4. The ultrasound diagnostic apparatus according to claim 1, wherein the second start point has an earlier start point that is temporally earlier than the first start point by predetermined number of sample points, and a later start point that is temporally later than the first start point by a predetermined number of sample point,
wherein the Doppler processor performs, in the second frequency analysis, frequency analysis using the complex data of the at least one second sample point group including the set number of sample points starting from the earlier start point and performs frequency analysis using the complex data of the at least one second sample point group including the set number of sample points starting from the later start point.

5. The ultrasound diagnostic apparatus according to claim 1, further comprising a data memory configured to store complex data generated by the Doppler processor, and
an input device comprising hardware configured to specify the set number of sample points and a number of sample points between the first start point and the second start point,
wherein the Doppler processor performs frequency analysis on the complex data stored in the data memory based on the set number of sample points and the number of sample points between the first start point and the second start point that are specified through the input device.

6. The ultrasound diagnostic apparatus according to claim 1,
wherein the reception circuit includes an analog/digital converter for converting the reception signal outputted from the transducer array into a digital signal, and
a beam former for performing phasing addition on the reception signal that is converted into the digital signal.

7. The ultrasound diagnostic apparatus according to claim 1, further comprising a B-mode processor configured to generate a B-mode image based on the reception radio-frequency data generated by the reception circuit,
wherein the monitor displays the Doppler waveform image generated by the Doppler processor and the B-mode image generated by the B-mode processor.

8. A method for generating a Doppler waveform image, comprising the steps of:
transmitting an ultrasonic beam from a transducer array toward a subject,
generating reception radio-frequency data that has undergone phasing addition by processing a reception signal outputted from the transducer array having received an ultrasonic echo from the subject,
generating complex data by performing quadrature detection on the reception radio-frequency data,
performing a first frequency analysis using the complex data of a first sample point group that includes a preliminarily set number of sample points starting from a first start point and a second frequency analysis using the complex data of at least one second sample point group includes the preliminarily set number of sample points starting from a second start point that is different from the first start point to acquire a spectral signal corresponding to each pixel of a Doppler waveform image based on results of the first frequency analysis and the second frequency analysis,
generating the Doppler waveform image using the spectral signal, and
displaying the Doppler waveform image on a monitor,
wherein the first start point for one pixel and the first start point for another pixel adjacent to the one pixel are distanced from each other by a first number of sample points corresponding to a first gap between adjacent pixels, and
wherein a second number of sample points corresponding to a second gap between the first sample point group and one of the at least one second sample point group farthest from the first sample point group for each pixel is set to a value smaller than ½ of the first number of sample points.

9. An ultrasound diagnostic apparatus comprising:
a transducer array;
a transmission circuit configured to transmit an ultrasonic beam from the transducer array toward a subject,
a reception circuit configured to process a reception signal outputted from the transducer array having received ultrasonic echoes from the subject to generate reception radio-frequency data that has undergone phasing addition,
a Doppler processor configured to perform quadrature detection on the reception radio-frequency data generated by the reception circuit to generate complex data; to perform a first frequency analysis using the complex data of a first sample point group that includes a set number of sample points starting from a first start point and a second frequency analysis using the complex data of at least one second sample point group that includes the set number of sample points starting from a second start point that is different from the first start point; to acquire a spectral signal corresponding to each pixel of a Doppler waveform image based on results of the first frequency analysis and the second frequency analysis; and to generate the Doppler waveform image using the spectral signal, and
a monitor configured to display the Doppler waveform image generated by the Doppler processor,
wherein the first start point for one pixel and the first start point for another pixel adjacent to the one pixel are distanced from each other by a first number of sample points Np corresponding to a gap between adjacent pixels,
wherein adjacent sample point groups among the first sample point group and the at least one second sample point group are distanced from each other by a third number of sample points Nb, and
wherein assuming that $Np_{MAX}$ represents the maximum value of the first number of sample points Np, $PRF_{MAX}$ represents the maximum value of the pulse repetition frequency, $TS_{MAX}$ represents the maximum value of the sweep time of the Doppler waveform image, and PN represents the number of pixels along the time axis of the Doppler waveform image, the maximum value $Nb_{MAX}$ of the third number of sample points Nb is denoted as $$Nb_{MAX} = Np_{MAX}/2 < (PRF_{MAX} \times Ts_{MAX}/PN)/2.$$

* * * * *